United States Patent
Blochet

(10) Patent No.: US 9,820,329 B2
(45) Date of Patent: Nov. 14, 2017

(54) METHOD FOR MANAGING A WIRELESS LINK BETWEEN A FIRST DEVICE AND A SECOND DEVICE

(71) Applicant: GEMALTO SA, Meudon (FR)

(72) Inventor: Marc Blochet, Meudon (FR)

(73) Assignee: GEMALTO SA, Meudon (FR)

( * ) Notice: Subject to any disclaimer, the term of this patent is extended or adjusted under 35 U.S.C. 154(b) by 73 days.

(21) Appl. No.: 14/896,607

(22) PCT Filed: Jun. 6, 2014

(86) PCT No.: PCT/EP2014/061905
§ 371 (c)(1),
(2) Date: Dec. 7, 2015

(87) PCT Pub. No.: WO2014/195497
PCT Pub. Date: Dec. 11, 2014

(65) Prior Publication Data
US 2016/0143083 A1    May 19, 2016

(30) Foreign Application Priority Data
Jun. 7, 2013    (EP) .................................... 13305773

(51) Int. Cl.
*H04B 7/00* (2006.01)
*H04W 76/04* (2009.01)
(Continued)

(52) U.S. Cl.
CPC ........ *H04W 76/045* (2013.01); *H04B 13/005* (2013.01); *H04W 52/0209* (2013.01);
(Continued)

(58) Field of Classification Search
CPC ........... H04W 76/045; H04W 52/0209; H04W 84/18; H04B 12/005
(Continued)

(56) References Cited

U.S. PATENT DOCUMENTS

| | | | |
|---|---|---|---|
| 2008/0174554 A1 | 7/2008 | Zhao | |
| 2009/0233548 A1 | 9/2009 | Andersson | |

FOREIGN PATENT DOCUMENTS

| | | |
|---|---|---|
| WO | WO2005062236 A1 | 7/2005 |
| WO | WO2007096810 A1 | 8/2007 |
| WO | WO2010078386 A1 | 7/2010 |

OTHER PUBLICATIONS

"What you touch in yours; Smartban(13)001-11_eGO_project", ETSI Draft; 650, Route Des Lucioles; F-06921 Sophia-Antipolis; France, vol. smartban, May 28, 2013, pp. 1-19, XP014156138.
(Continued)

*Primary Examiner* — Brenda H Pham
(74) *Attorney, Agent, or Firm* — The Jansson Firm; Pehr B. Jansson

(57) ABSTRACT

The invention relates to a method for managing a wireless link between a first device and a second device. The method includes the steps of polling an activity of a first wireless interface of the first device during a first predetermined lapse of time, suspending the wireless link and polling an activity of a first body-coupled communication interface of the first device during a second predetermined lapse of time when no activity is detected on the first wireless interface of the first device during the first predetermined lapse of time, and resuming the wireless link when at least one polling packet comprising a resume request is detected by the first body-coupled communication interface of the first device during the second predetermined lapse of time.

19 Claims, 1 Drawing Sheet

(51) Int. Cl.
*H04B 13/00* (2006.01)
*H04W 52/02* (2009.01)
*H04W 84/18* (2009.01)
*A61B 5/00* (2006.01)

(52) U.S. Cl.
CPC .......... *H04W 84/18* (2013.01); *A61B 5/0028* (2013.01); *Y02B 60/50* (2013.01)

(58) Field of Classification Search
USPC .......................................... 370/310, 311, 318
See application file for complete search history.

(56) References Cited

OTHER PUBLICATIONS

PCT/EP2014/061905, International Search Report, dated Aug. 21, 2014, European Patent Office, P.B. 5818 Patentlaan 2 NL-2280 HV Rijswijk.
PCT/EP2014/061905, Written Opinion of the International Searching Authority, dated Aug. 21, 2014, European Patent Office, P.B. 5818 Patentlaan 2 NL-2280 HV Rijswijk.
"What you touch is yours; Smartban(13)001011_eGO_project", ETSI Draft; 650, Route Des Lucioles; F-06921 Sophia-Antipolis; France, vol. smartban, May 28, 2013, pp. 1-19, XP014156138, the whole document.

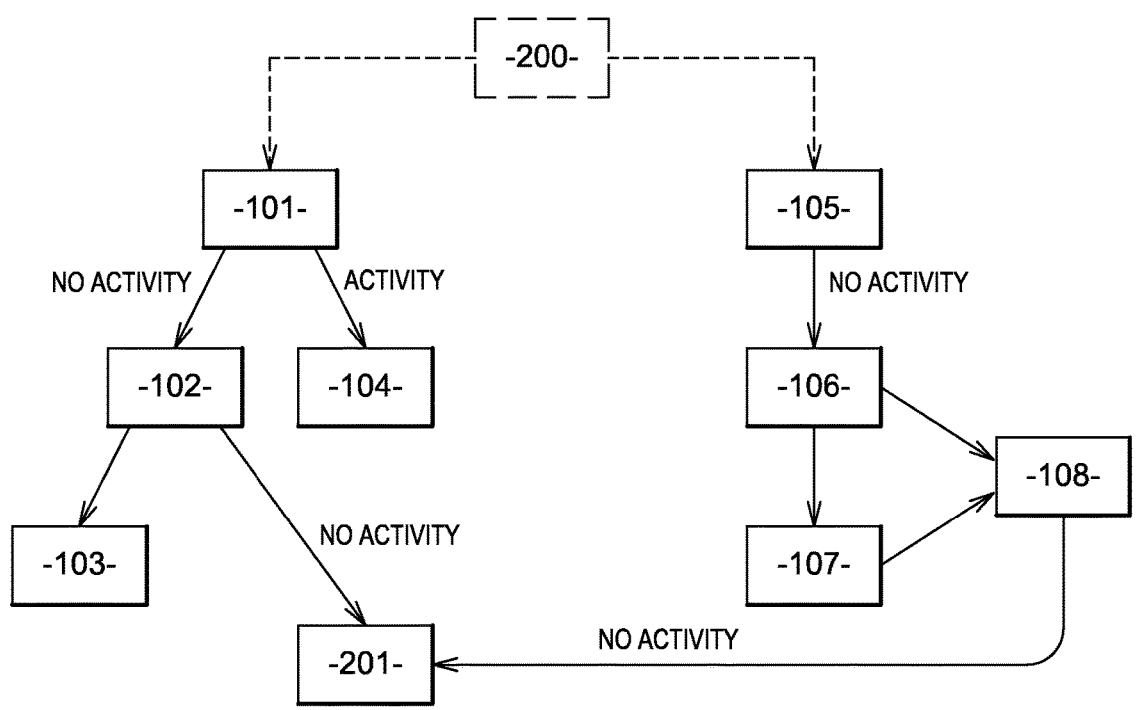

METHOD FOR MANAGING A WIRELESS LINK BETWEEN A FIRST DEVICE AND A SECOND DEVICE

FIELD OF THE INVENTION

The invention relates to a method for managing a wireless link between a first device and a second device, said first and second device communicating with each other through the wireless link and an alternate out-of-band link, especially a body-coupled communication (BCC) link.

TECHNICAL BACKGROUND

Usually, when a link is established between two devices, upper protocol layers create logical connections and data contexts associated with these connections. For example, once a Bluetooth link has been created; upper layers such as L2CAP, RFCOMM, BNEP, and TCPIP create logical channels and maintain session contexts. The applications themselves create specific contexts. Contexts of interest are also the security contexts built for message encryption, message integrity, authentication, identification and authorization purpose. Each protocol layer expects a link manager to maintain the link available between said two devices. If the link is lost, they expect to be notified of the link down event.

During periods of inactivity, when there is no transfer of data between the two devices through the link, the link manager periodically sends polling packets in order to have the assurance that the link between the devices is still operational and also to maintain a synchronization between the two devices in order to allow an active communication to be re-established when needed.

However, the sending of poll packets through a wireless link for a long time is likely to be costly in terms of energy use.

Contactless devices are widely used for authentication. Individuals have a need for a unique contactless device comprising as much authentication information as possible for executing secure electronic transactions, logins on mobile device etc. . . , without having to remember all of them.

The applicant has thus developed personal contactless devices allowing an individual to have in the same device a lot of authentication information, said device being wearable by individuals and having a body-coupled communication interface. The contactless device can be on a bracelet, an ankle, a belt, a garment, in a pocket etc. . .

The authentication is easy to perform for the user. Indeed, when a user, wearing said contactless device, touches (or is close enough) to a device to which the user has to be authenticated, the authentication is performed by the contactless device without any further action than the touching action to be performed by the user wearing the contactless device.

For example, when a user wearing said kind of contactless devices touches the doorknob of a door, said doorknob being able to communicate with the contactless device, it opens said door.

The contactless device communicates through the skin of the user with the device to which the user wants to authenticate. This kind of communication is named body-coupled communication (BCC). The BCC is based on the principle that modulated electric field may carry a signal on a user body according to a capacitive coupling mode, thus the human body, and more particularly the skin, is used as a wire between the contactless device and a device with which it communicates with to ensure authentication of the user.

The contactless device is connected to a proxy and said proxy is connected to a device to which the authentication has to be performed.

The first device is powered by a battery and the second device is fully powered by a power supply.

Usually, the communication between a contactless device and its associated proxy follows the following scheme: the user wearing the contactless device touches the proxy, by this touch the proxy and the contactless device can exchange a secret information through a BCC path, and then a secure wireless communication path, based on this secret information, is established between the proxy and the contactless device to exchange another set of data allowing the authentication of the user wearing the contactless device on the device connected to the proxy. The secret information allows the pairing of the devices.

There are two main use cases of these contactless devices:
  short-lived use cases. For example, when the contactless device is used to open a door (or allow an e-payment), it has to authenticate itself (and thus the user wearing the contactless device) only once to allow the opening of the door (or the achievement of the e-payment). Thus, once the other set of data has been exchanged through the wireless communication path, the communication is terminated by closing the path. Hence, the communication between the contactless device and the proxy/the door in this use case is a short-lived one; and
  long-lived use cases, for which the wireless communication path has to remain open much longer, for example when the contactless device is used to allow a login on a computer. The proxy is connected to the computer; the contactless device is worn by a user. The proxy emulates a card reader and the contactless device emulates the card to be read, said card comprising authentication information. The reading of the emulated card by the emulated card reader allows the login on the computer and the opening of a secure session. But, the card has to remain in the card reader as long as the user wants to keep its session open on the computer, thus the wireless communication has to remain active as long as the user wants to remain logged on its session.

Contactless devices are battery-powered devices and as they are aimed to be worn by users, their small size induces low capacity battery. Hence, maintaining the wireless communication between the proxy and the battery-powered contactless device for long-lived use cases is highly energy consuming and reduces consequently the lifespan of contactless devices.

SUMMARY

It is an object of the invention to provide an alternative solution to maintain the wireless communication active between a contactless device and its associated proxy and ensuring a reduction of the energy consumption of said devices.

To this end, the invention provides a method for managing a wireless link between a first device and a second device, said method comprising the steps of:
  polling an activity of a first wireless interface of the first device during a first predetermined lapse of time;
  suspending the wireless link and polling an activity of a first body-coupled communication interface of the first device during a second predetermined lapse of time when no activity is detected on the first wireless interface of the first device during the first predetermined lapse of time;

resuming the wireless link when at least one polling packet comprising a resume request is detected by the first body-coupled communication interface of the first device during the second predetermined lapse of time.

If there is no exchange of data on the wireless link, meaning no activity is detected on the first wireless interface, during the first predetermined lapse of time, the first device suspends the wireless link and verifies if there is an activity between the first body-coupled communication interface of the first device and a second body-coupled communication interface of the second device. It is through the body-coupled communication link that the polling packet to maintain and/or resume the wireless link is to be transmitted. Thus, by polling an activity on the first BCC interface of the first device, the first device has the role of a listener, listening to potential polling packet sent by the second device. If the BCC link allows a bi-directional communication, the first device may optionally send polling packets to the second device through the BBC link.

The use of an alternate body-coupled communication link between the two connected devices to exchange the poll packets used to detect loss of connectivity during the inactivity periods allows the power resource constrained device to resume the wireless link only when this is necessary, in particular when a resume request is received in a polling packet, thus allowing a reduction of the energy consumption of the devices, as a wireless link is more energy-consuming to maintain than a BCC link.

The steps of polling an activity of the first wireless interface and of the first BCC interface of the first device are performed by calculators (or the same calculator) of the first device. The step of resuming the wireless link when a polling packet is detected by the first BCC interface is preferably performed by a wireless controller of the first wireless interface of the first device.

According to not limited embodiments, the method can comprise one or more of the following additional characteristics:

- the method comprises a step of polling for a link suspend on a second wireless interface of the second device during a third predetermined lapse of time. This step is preferably performed by a calculator of the second device;
- the method comprises a step of generating polling packets by a second body-coupled communication interface of the second device when the link is suspended on the second wireless interface of the second device during the third predetermined lapse of time. This step is preferably performed by a calculator of the second device;
- the method comprises a step of generating at least a polling packet comprising a resume request by the second body-coupled communication interface of the second device when the second device has data to send to the first device through the wireless link. This step is preferably performed by a calculator of the second device;
- the method comprises a step of polling for a link resume on the second wireless interface or an activity of the second BCC interface during a fourth predetermined lapse of time after the generation of the polling packet. This step is preferably performed by a calculator of the second device;
- the method comprises a preliminary step of pairing the first device and the second device in order to establish the wireless link between the first device and the second device and a step of maintaining said wireless link during a fifth lapse of time by iterating the method according to any one of the preceding embodiments;
- the method comprises a step of terminating the communication between the two devices when:
  - no activity is detected on the first body-coupled communication interface of the first device during the second predetermined lapse of time or no activity is detected on the second wireless interface or the second BCC interface during a third and fourth predetermined lapse of time;
- the first device is a contactless device being configured to contain a user's personal information in order for said user to authenticate itself to a secure system and wherein the second device is a proxy between the first device and the secure system. The step of pairing the first device and the second device allows the user's connection to the secure system and the steps of polling activities allows the wireless link established to be maintained between the first device and the second device;
- the second device is a proxy between the first device and the secure system;
- the first device is powered by a battery and the second device is fully powered by a power supply.

The invention also concerns a system for the implementation of the method according to any one of the previously described embodiments, said system comprising a contactless device and a proxy for the managing of a wireless link between the contactless device and the proxy.

BRIEF DESCRIPTION OF THE DRAWINGS

Some embodiments of method in accordance with embodiments of the present invention are now described, by way of example only, and with reference to the accompanying drawing, in which:

FIG. 1 schematically illustrates an embodiment of a method according to an embodiment of the invention;

Like reference characters denote like elements throughout figures and text.

DESCRIPTION OF EMBODIMENTS

Referring now to the drawings, FIG. 1 illustrates the steps of a method for managing a wireless link between a first device and a second device.

The first device comprises a first wireless interface and the second device comprises a second wireless interface. The first wireless interface and the second wireless interface allow the definition of a wireless path between the first device and the second device. A wireless link could be established through the wireless path.

The first device also comprises a first BCC interface and the second device comprises a second BCC interface. The first BCC interface and the second BCC interface allow the definition of a BCC path between the first device and the second device. A BCC link could be established through the BCC path.

In this embodiment the first device is a contactless device configured to contain a user's personal information. Said personal information is used to authenticate the user to a secure system, for example a computer, a mobile device, a building. The second device in this embodiment is a proxy between the first device and the secure system to which the user wants to authenticate. The second device ensures the communication between the first device which is BCC compliant and the secure system which is not obviously BCC compliant.

The first device is configured to be worn, in use, by the user. Indeed the first device uses its BCC interface to interact with the second device and establish a wireless link in a secure way through the wireless path between the first and the second device. The wireless link is established between the first wireless interface of the first device and the second wireless interface of the second device. In order to establish this wireless link in a secure way, a preliminary step of pairing 200 is performed between the first device and the second device via the BCC path. A BCC transmission (BCC communication) is less energy-consuming than a wireless transmission but the transmission speed is correlated to the energy-consumption of these transmissions: the transmission speed of a wireless transmission is higher than the transmission speed of a BCC transmission. The wireless link could use various wireless protocols such as Zigbee, Bluetooth or Wi-Fi for example.

The skin of the user acts as an antenna to establish the BCC communication between the first device, worn by the user, and the second device when the skin of the user is close enough to the second device. The degree of how close enough the skin of the user has to be to the second device depends on the second BCC interface of the second device (it's the same regarding the distance between the first device and the skin of the user). The dimensioning of the component of the second BCC interface (and of the first BCC interface) determines the distance necessary between the second device and the skin of the user (and the first device and the skin of the user) to establish a BCC link.

In this embodiment, the second device, acting as a proxy, is a mouse of a computer and the secure system to which a user needs to authenticate himself, is said computer. The use case of this embodiment is the logging of the user on a user session of the computer. This logging must be maintained as long as the user wearing the first device wants to stay logged on the computer.

The method for managing the wireless link between the first device and the second device comprises a step of polling an activity 101 of a first wireless interface of the first device during a first predetermined lapse of time T1. By polling an activity on the first interface (or on any interface), one must understand checking if any data is sent or received by said interface. The step of polling an activity 101 of the first wireless interface of the first device enables to check if the first device, the contactless device in this embodiment, receives data through the wireless link from the proxy or sends data through the wireless link to the proxy. If an activity is detected, it means that the wireless link is in use. The first predetermined lapse of time T1 is predetermined according to technical specification and/or constraints. In particular while in activity 101, the communication latency is low, while in activity 102 the communication latency is higher due to a necessary resume of the wireless link.

When no activity is detected on the first wireless interface during the first predetermined lapse of time T1, the wireless link is suspended and a step of polling an activity 102 of the first BCC interface of the first device during a second undefined lapse of time T2 is performed. This step aims to check if the first device receives data through the BCC link. These data could be polling packets from the second device sent to maintain the communication on between the first device and the second device.

When a polling packet is received on the first BCC interface of the first device, the first device may answer by sending back a polling packet on the first BCC interface to ensure the second device of the presence of the first device (assuming the BBC link is bi-directional). The first device may also resume the wireless link and either sends data through the wireless link or waits for the second device to send data.

If during T2 the first device does not receive poll packets on the first BCC interface after a predetermined lapse of time, the first device may either terminates the communication or may try to resume the wireless link to check is the communication is still active.

When no activity is detected on the first wireless interface, the first device could put on stand-by/sleeping mode the first wireless interface in order to save energy of the first device, which in this embodiment is powered by a battery, and since the first device is aimed to be worn by a user, its small size induce a small battery, so saving energy is crucial.

The method comprises a step of resuming the wireless link 103 when at least one polling packet comprising a resume request is detected by the first BCC interface of the first device during the second predetermined lapse of time T2. It means that the second device wants to perform a transmission through the wireless link and thus the first device has to wake up its first wireless interface. Polling packet comprising a resume request is sent through the BCC link as this connection is maintained between the two devices instead of the wireless link because of energy-saving consideration.

If an activity is detected on the first wireless interface of the first device during the first predetermined lapse of time T1, the first BCC interface of the first device could be placed 104 in a stand-by mode. Placing the first BCC interface in a stand-by mode when there is activity on the first wireless interface implies that the BCC interface, and thus the BCC link, is used only to transfer poling packets to maintain the wireless link active between the first device and the second device. This step of placing 104 the first BCC interface in a stand-by mode is not statutory as the BCC link could be used for the transfer of other information than information, like polling packets, to maintain the wireless link active.

Now referring in the perspective of the second device, the method comprises a step of polling for a link suspend on the second wireless interface of the second device 105 during the first predetermined lapse of time T1. When a link suspend is received on the second wireless interface of the second device, a step of generating a polling packet by a second BCC interface of the second device 106 is performed during a third predetermined lapse of time T3. This polling packet is a packet of data acting like a PING request in order to inform the first device that the second device is still present and ready to use the wireless link if needed. The polling packet is sent over the BCC link in order to reduce the energy consumption of the first device. The polling packet may contain the address of the second device, integrity information, and eventually a resume request when the second device intends to reactivate the wireless link. In this case, when the second device has data to send to the first device through the wireless link, the method comprises a step of generating at least a polling packet comprising a resume request by the second BCC interface of the second device 107. The BCC link is still used to perform this step in order to reduce energy-consumption of the method and of the associated devices.

After the generation of the polling packet, comprising a resume request to resume the wireless link or not (to just maintain the wireless link available between the first device and the second device), the second device waits for an answer of the first device.

In case, the second device has generated a polling packet comprising a resume request, a step of polling an activity of the second wireless interface of the second device 108 is performed during a predetermined lapse of time Tresume.

Indeed, a polling packet comprising a resume request intends to reactivate the wireless link.

In case, the second device has generated a polling packet, not necessary comprising a resume request, a step of polling an activity either of the second BCC interface or of the second wireless interface is performed. The answer of the first device depends on whether the first device only answers by sending back a polling packet to ensure the second device of the presence of the first device or the first device resumes the wireless link and sends data through the wireless link.

By iterating the steps previously described by both the first device and the second device, the wireless link can be maintained between the first device and the second device thanks to the use of the BCC link to transmit the polling packets.

The method comprises a step of terminating the communication between the two devices 201 when:
No activity is detected on the first body-coupled communication interface of the first device during the second predetermined lapse of time (T2) or no activity is detected on the second wireless interface or the second BCC interface during a third and fourth predetermined lapse of time (T3/T4)

This method has been described according to an embodiment wherein the first device is a contactless device and the second device is a proxy between the first device and a secure system. But the role of the first device and of the second device may be switched meaning, the second device is a contactless device being configured to contain a user's personal information in order for said user to authenticate itself to a secure system and the second device is a proxy between the first device and the secure system.

Unless otherwise specified, the order in which the steps are performed does not matter.

The invention claimed is:

1. A method for managing a wireless link between a first device and a second device, said method comprising the steps of:
    polling an activity of a first wireless interface of the first device (101) during a first predetermined lapse of time (T1);
    suspending the wireless link and polling an activity of a first body-coupled communication interface of the first device (102) during a second predetermined lapse of time (T2) when no activity is detected on the first wireless interface of the first device during the first predetermined lapse of time;
    resuming the wireless link (103) when at least one polling packet comprising a resume request is detected by the first body-coupled communication interface of the first device during the second predetermined lapse of time (T2).

2. The method according to claim 1, comprising a step of polling for a link suspend on a second wireless interface of the second device (105) during the first predetermined lapse of time (T1).

3. The method according to claim 1, comprising a step of generating polling packets by a second body-coupled communication interface of the second device (106) when the link is suspended on the second wireless interface of the second device during a third predetermined lapse of time (T3).

4. The method according to claim 3 comprising a step of generating at least a polling packet comprising a resume request by the second body-coupled communication interface of the second device (107) when the second device has data to send to the first device through the wireless link.

5. The method according to claims 3 comprising a step of polling for a link resume on the second wireless interface of the second device (108) during a fourth predetermined lapse of time (T4) after the generation of the polling packet.

6. The method according to claim 3, comprising a step of polling an activity of the second BCC interface of the second device (109) during the fourth (T4) predetermined lapse of time after the generation of the polling packet.

7. The method according to claim 1, comprising a preliminary step of pairing (200) the first device and the second device in order to establish the wireless link between the first device and the second device and a step of iterating the method according to claim 1 in order to maintain said wireless link.

8. The method according to claim 1 comprising a step of terminating the communication between the two devices when:
    no activity is detected on the first body-coupled communication interface of the first device during the second predetermined lapse of time (T2) or no activity is detected on the second wireless interface or the second BCC interface during a third and fourth predetermined lapse of time (T3/T4).

9. The method according to claim 1 wherein the first device is a contactless device being configured to contain a user's personal information in order for said user to authenticate itself to a secure system and wherein the second device is a proxy between the first device and the secure system.

10. The method according to claim 1 wherein the second device is a proxy between the first device and the secure system.

11. The method according to claim 1, wherein the first device is powered by a battery and the second device is fully powered by a power supply.

12. The method according to claim 2, comprising a step of generating polling packets by a second body-coupled communication interface of the second device (106) when the link is suspended on the second wireless interface of the second device during a third predetermined lapse of time (T3).

13. The method according to claim 12 comprising a step of generating at least a polling packet comprising a resume request by the second body-coupled communication interface of the second device (107) when the second device has data to send to the first device through the wireless link.

14. The method according to claims 4 comprising a step of polling for a link resume on the second wireless interface of the second device (108) during a fourth predetermined lapse of time (T4) after the generation of the polling packet.

15. The method according to claim 4, comprising a step of polling an activity of the second BCC interface of the second device (109) during the fourth (T4) predetermined lapse of time after the generation of the polling packet.

16. The method according to claim 2, comprising a preliminary step of pairing (200) the first device and the second device in order to establish the wireless link between the first device and the second device and a step of iterating the method according to claims 1 and 2 in order to maintain said wireless link.

17. The method according to claim 2 comprising a step of terminating the communication between the two devices when:
- no activity is detected on the first body-coupled communication interface of the first device during the second predetermined lapse of time (T2) or no activity is detected on the second wireless interface or the second BCC interface during a third and fourth predetermined lapse of time (T3/T4).

18. The method according to claim 2 wherein the first device is a contactless device being configured to contain a user's personal information in order for said user to authenticate itself to a secure system and wherein the second device is a proxy between the first device and the secure system.

19. The method according to claim 2, wherein the first device is powered by a battery and the second device is fully powered by a power supply.

* * * * *